United States Patent
Callens et al.

(10) Patent No.: US 7,538,245 B2
(45) Date of Patent: May 26, 2009

(54) PROCESS FOR THE MANUFACTURE OF AN ENANTIOPURE COMPOUND

(75) Inventors: Roland Callens, Grimbergen (BE); Georges Blondeel, Aalst (BE); Cyrille Pousset, Brussels (BE); Ronan Gire, Brussels (BE)

(73) Assignee: Solvay S.A. (BE)

( * ) Notice: Subject to any disclaimer, the term of this patent is extended or adjusted under 35 U.S.C. 154(b) by 0 days.

(21) Appl. No.: 10/570,933

(22) PCT Filed: Sep. 8, 2004

(86) PCT No.: PCT/EP2004/052094

§ 371 (c)(1),
(2), (4) Date: Mar. 8, 2006

(87) PCT Pub. No.: WO2005/023838

PCT Pub. Date: Mar. 17, 2005

(65) Prior Publication Data

US 2007/0027326 A1 Feb. 1, 2007

(30) Foreign Application Priority Data

Sep. 9, 2003 (FR) .................................. 03 10582

(51) Int. Cl.
*C07C 51/42* (2006.01)
(52) U.S. Cl. ...................... 562/608; 562/600
(58) Field of Classification Search ........................ None
See application file for complete search history.

(56) References Cited

U.S. PATENT DOCUMENTS 4,097,490 A * 6/1978 Reinhold ..................... 548/534
4,725,645 A 2/1988 Anteunis et al.
7,138,538 B2 * 11/2006 Delplanche et al. ........... 560/19

FOREIGN PATENT DOCUMENTS

EP 0 184 243 6/1986
EP 0 206 283 12/1986

OTHER PUBLICATIONS

Anteunis, M. J. O., et al., "Preparation of (s) -2-Methylbutylamine and Synthesis of Chiral Isoleucine and Alloisoleucine", Bull. Soc. Chim. Belge, 1987, vol. 96, No. 7, pp. 545-553.
Eliel, E. L., et al., "Stereochemistry of Organic Compounds", Wiley-Interscience Publication, 1994, pp. 322-340.
Swan, J. M., et al., "The Synthesis of L-Gluraminyl-L-Asparagine, L-Glutamine and L-Isoglutamin from p-Toluenesulfonyl-L-Glutamic Acid", J. Amer. Chem. Soc., 1954, vol. 76, pp. 3110-3113.
Rudinger, J., et al., "Amino-Acids and Peptides X some Derivatives and Reactions of 1-p-Toluenesulphonyl-L-Pyrrolid-5-One Carboxylic Acid", Collect Czech Chem. Commun., 1954, vol. 1954, pp. 365-373.
Berse, C., et al., "Tosylated Peptides and p-Nitrophenyl Esters", Canadian Journal of Chemistry, 1963, vol. 41, No. 11, pp. 2767-2773.

* cited by examiner

*Primary Examiner*—Karl J Puttlitz
(74) *Attorney, Agent, or Firm*—Connolly Bove Lodge & Hutz LLP

(57) ABSTRACT

Process for the manufacture of an enantiopure compound comprising at least one functional group capable of reacting with an activated carboxyl group, starting from a mixture of enantiomers of the said compound, in which process: (a) a reaction medium comprising the mixture of enantiomers and a reagent based on an enantiopure amino acid, in which reagent at least one amino group of the amino acid is protected by a protective group and in which reagent at least one carboxyl group of the amino acid is activated, is subjected to conditions appropriate for bringing about the reaction of the functional group capable of reacting with the activated carboxyl group with the activated carboxyl group, so as to form a carbonyl bond; (b) the mixture of diastereomers obtained is subjected to a separation operation, so as to obtain at least one fraction composed essentially of a diastereomer, (c) at least a portion of the said fraction is subjected to a stage of cleavage of the carbonyl bond under conditions under which the protective group is essentially stable; and (d) the enantiopure compound and an enantiopure derivative of the amino acid in which at least one amino group is protected by the protective group are recovered.

20 Claims, No Drawings

US 7,538,245 B2

PROCESS FOR THE MANUFACTURE OF AN ENANTIOPURE COMPOUND

RELATED APPLICATIONS

This application is a national stage application (under 35 U.S.C. 371) of PCT/EP2004/052094 filed Sep. 8, 2004 which claims benefit to French application 0310582 filed Sep. 9, 2003.

The invention relates to a process for the manufacture of an enantiopure compound.

The production of enantiopure compounds is a matter of great importance in the pharmaceutical, chemical and biotechnology industries. This is because the two enantiomers of a chemical substance with an identical composition can have radically different biological activities. It is thus desirable to have available separation reagents and techniques which make it possible to separate the enantiomers and to analyse the enantiomeric purity of pharmaceutical, chemical and biotechnology products. It is particularly desirable to have available processes which make possible the manufacture on a preparative scale of a desired enantiomer, for example starting from a racemic mixture of enantiomers.

Patent Application EP-A-206 283 discloses the separation of 7,8-difluoro-2,3-dihydro-3-methyl-4H-[1,4]benzoxazine enantiomers by derivatization with (S)-N-tosylproline chloride, followed by various separation operations.

It was desirable to have available a process which makes possible the manufacture of a large number of enantiopure compounds, in particular of enantiopure amino acids, in an economic way, in particular as regards the yields and purities of enantiopure compounds and the overall economics of the process.

The invention is targeted at overcoming these problems.

The invention consequently relates to a process for the manufacture of an enantiopure compound comprising at least one functional group capable of reacting with an activated carboxyl group, starting from a mixture of enantiomers of the said compound, in which process (a) a reaction medium comprising the mixture of enantiomers and a reagent based on an enantiopure amino acid, in which reagent at least one amino group of the amino acid is protected by a protective group and in which reagent at least one carboxyl group of the amino acid is activated, is subjected to conditions appropriate for bringing about the reaction of the functional group capable of reacting with the activated carboxyl group with the activated carboxyl group, so as to form a carbonylic bond;

(b) the mixture of diastereomers obtained is subjected to a separation operation, so as to obtain at least one fraction composed essentially of a diastereomer;

(c) at least a portion of the said fraction is subjected to a stage of cleavage of the carbonylic bond under conditions under which the protective group is essentially stable; and (d) the enantiopure compound and an enantiopure derivative of the amino acid in which at least one amino group is protected by the protective group are recovered.

It has been found, surprisingly, that the process according to the invention makes it possible to obtain good results for the preparation of enantiomers comprising at least one functional group capable of reacting with the activated carboxyl group. The process according to the invention is particularly economic as the consumption of enantiopure reagent necessary for the separation of the enantiopure compound can be limited by virtue of the recovery of the enantiopure derivative of the protected amino acid, which can be readily reused.

The term "amino acid" is intended to denote, for the purposes of the present invention, any compound comprising at least one amino group, in particular an $NH_2$ group, and at least one carboxyl group. The amino acids used in the present invention are chiral amino acids comprising at least one asymmetric carbon. Use may be made of any chiral amino acid well known per se of natural or synthetic origin.

The term "carbonylic bond" is intended to denote, for the purposes of the present invention, in particular a bond between the carbon atom of a carbonyl group and an atom of the compound comprising at least one functional group capable of reacting with an activated carboxyl group.

Examples of reagents according to the invention are based, for example, on the following natural amino acids:

alanine, valine, norvaline, leucine, norleucine, isoleucine, serine, isoserine, homoserine, threonine, allothreonine, methionine, ethionine, glutamic acid, pyroglutamic acid, aspartic acid, asparagine, cysteine, cystine, phenylalanine, tyrosine, tryptophan, lysine, arginine, histidine, ornithine, glutamine and citrulline.

The unnatural enantiomers can also be used.

Examples of amino acids of synthetic origin which can be used as basis for the reagent according to the invention comprise, for example, the following amino acids:

(1-naphthyl)alanine, (2-naphthyl)alanine, homophenylalanine, (4-chlorophenyl)alanine, (4-fluorophenyl)alanine, (3-pyridyl)alanine, phenylglycine, diaminopimelic acid (2,6-diaminoheptane-1,7-dioic acid), 2-aminobutyric acid, 2-aminotetralin-2-carboxylic acid, erythro-β-methylphenylalanine, threo-β-methylphenylalanine, (2-methoxyphenyl)alanine, 1-amino-5-hydroxyindane-2-carboxylic acid, 2-aminoheptane-1,7-dioic acid, (2,6-dimethyl-4-hydroxyphenyl)alanine, erythro-β-methyltyrosine or threo-β-methyltyrosine.

The term "enantiopure amino acid" is intended to denote a chiral amino acid essentially composed of one enantiomer. The enantiomeric excess (ee) is defined: ee $(\%) = 100(x_1 - x_2)/(x_1 - x_2)$ with $x_1 > x_2$; $x_1$ and $x_2$ represent the content of enantiomer 1 or 2 respectively in the mixture.

Use is generally made of an enantiopure amino acid having an enantiomeric excess of greater than or equal to 99%. Preference is given to an enantiopure amino acid having an enantiomeric excess of greater than or equal to 99.5%. In a particularly preferred way, use is made of an enantiopure amino acid having an enantiomeric excess of greater than or equal to 99.9%.

Any enantiopure amino acid can be used as basis for the reagent according to the invention. Preferably, the enantiopure amino acid is selected from the abovenamed amino acids of natural or synthetic origin. In a particularly preferred way, the enantiopure amino acid is selected from proline, glutamic acid and pyroglutamic acid, which are optionally substituted. Pyroglutamic acid is very particularly preferred. In a specific example, the reagent is based on (2S)-pyroglutamic acid.

In the process according to the invention, at least one amino group of the reagent is protected by a protective group.

Mention may in particular be made, as nonlimiting examples of protective groups for the amino functional group, of substituted or unsubstituted groups of alkyl or aralkyl type, such as the benzyl, diphenylmethyl, di(methoxyphenyl)methyl or triphenylmethyl (trityl) group, substituted or unsubstituted groups of acyl type, such as the formyl, acetyl, trifluoroacetyl, benzoyl or phthaloyl group, substituted or unsubstituted groups of aralkyloxycarbonyl type, such as the benzyloxycarbonyl, p-chlorobenzyloxycarbonyl, p-bromobenzyloxycarbonyl, p-nitrobenzyloxycarbonyl, p-methoxybenzyloxycarbonyl, benzhydryloxycarbonyl, 2-(p-biphenylyl)isopropyloxyearbonyl, 2-(3,5-dimethoxyphenyl)isopropyloxy-carbonyl, p-phenylazobenzyloxycarbonyl, triphenylphosphonoethyloxycarbonyl or 9-fluorenylmethyloxycarbonyl group, substituted or unsubstituted groups of alkyloxycarbonyl type, such as the tert-butyloxycarbonyl, tert-amyloxycarbonyl, diisopropylmethyloxycarbonyl, isopropyloxycarbonyl, ethyloxycarbonyl, allyloxycarbonyl or 2,2,2-trichloroethyloxycarbonyl group, or groups of cycloalkyloxycarbonyl type, such as the cyclopentyloxycarbonyl, cyclohexyloxycarbonyl, adamantyloxycarbonyl or isobornyloxycarbonyl group.

The protective group is often a sulphonyl group, in particular an alkylsulphonyl or arylsulphonyl group, preferably an arylsulphonyl group.

It has been found that sulphonyl groups, in particular (hetero)arylsulphonyl groups, make possible a particularly effective recovery of the N-sulphonyl derivative of the enantiopure amino acid while making possible a quantitative and essentially racemization-free recovery of the enantiopure compound.

Typical arylsulphonyl groups employed in the reagent comprise from 6 to 24 carbon atoms and are chosen, for example, from the benzenesulphonyl, naphthylsulphonyl, anthracenylsulphonyl, fluorenylsulphonyl and anthraquinonylsulphonyl groups, which are optionally substituted. Specific examples are chosen from the p-toluenesulphonyl (tosyl), mesitylenesulphonyl or methoxytrimethylphenylsulphonyl group. The p-toluenesulphonyl group is preferred.

In the process according to the invention, at least one carboxyl group in the reagent is activated.

The activated group can, for example, be an acid halide or an anhydride. Mention may be made, among acid halides, of acid fluorides, acid chlorides and acid bromides. Use is preferably made of an acid chloride.

In a first embodiment, the reagent comprising the carboxyl group activated beforehand is employed as is in the process according to the invention.

In a second embodiment, the carboxyl group of the reagent is activated in situ, that is to say by an activating compound present in the reaction medium. An example of such a method is the activation of the carboxyl group by DCC (dicyclohexylcarbodiimide), optionally with a coactivant, such as HOBT (hydroxybenzotriazole).

The reagent employed in the process according to the invention can be obtained from the respective enantiopure amino acid by methods known per se. It is possible, for example, to introduce a sulphonyl group by reaction with a corresponding sulphonyl halide. The carboxyl group can, for example, be converted to the acid chloride by reaction with $PCl_5$.

In the process according to the invention, the reagent according to the invention is reacted with a mixture comprising at least enantiomers comprising at least one functional group capable of reacting with the activated carboxyl group.

The functional group capable of reacting with the activated carboxyl group is often an amino group, which is optionally monoalkylated, a hydroxyl group or a thiol group.

In this case, amide, ester or thioester bonds are respectively obtained as carbonylic bond.

When the functional group capable of reacting with the activated carboxyl group is an amino group, use is advantageously made of a persilylated derivative of the compound comprising this group, which can be obtained, for example, according to the procedure disclosed in Application EP 184 243.

The enantiomers comprising at least one functional group capable of reacting with the activated carboxyl group which can be separated by the process according to the invention are generally amino acids, primary or secondary amines, peptides, alcohols, hydroxy acids or thiols. The process according to the, invention gives good results in separating the enantiomers of amino acids, such as, for example, the amino acids of natural or synthetic origin mentioned above.

In a first particularly preferred embodiment, the process according to the invention applies to the production of an enantiopure α-amino acid.

In a second particularly preferred embodiment, the process according to the invention applies to the production of an enantiopure β-amino acid. The process according to the invention can also be employed for the production of other amino acids exhibiting a greater distance between the amino group and the carboxyl group, such as γ-, δ- or ε-amino acids. The process according to the invention is suitable for the production of cyclic or acyclic amino acids, it being possible for the amino group to be present within a heterocycle.

Specific examples of β-amino acids which can be obtained according to the process according to the invention are chosen, for example, from β-homovaline, β-homophonylalarnie, β-homophenylglycine, β-homo(3'-pyridyl)glycine, β-homoalanine, ε-trifluoroacetyl-β-homolysine, β-homolysine, β-homoaspartic acid, β-homoproline and 2-piperidineacetic acid.

The process according to the invention also gives good results in separating a mixture of enantiomers of imino acids. The term "imino acid" is intended to denote any compound comprising at least one NHR group, in which R represents an organic radical, such as, for example, an alkyl or aryl radical, and at least one carboxyl group.

The imino acid can be aliphatic, e.g of formula HOOC—CnH2n—NHR with n>1, e.g. from 2 to 12, in which C—H bonds can be substituted e.g. by functional groups or halogen. In this case, R is suitably selected from C1-C4 alkyl groups or optionally substituted phenyl. N-methylvaline is an example of such an aliphatic iminoacid.

The iminoacid can also contain the secondary amine group embedded in a heterocycle. In this case, the cycle containing the imino group is generally formed by 3, 4, 5, 6 or 7 atoms, preferably from 5, 6 or 7 atoms. The heterocycle can be substituted and/or be part of a fused ring system.

Such heterocyclic imino acids are, for example, those belonging to the group consisting of proline, pipecolic acid (piperidine-2-carboxylic acid), morpholine-3-carboxylic acid, piperazine-2-carboxylic acid, 1-thia-4-azacyclo-hexane-3-carboxylic acid, α-methylproline, cis-4-hydroxyproline, baikaine (1,2,3,5-tetrahydropyridine-2-carboxylic acid), cis-4-hydroxypipecolic acid, trans-5-hydroxypipecolic acid, 1,2,3,4-tetrahydronorharman-1-carboxylic acid, 1,2,3,4-tetrahydro-6-hydroxyisoquinoline-3-carboxylic acid, 1,2,3,4-tetrahydro-isoquinoline-3-carboxylic acid, and 1,2,3,4-tetrahydroisoquinoline-1-carboxylic acid.

In a third particularly preferred embodiment, the process according to the invention applies to the production of an enantiopure alcohol. The alcohol is preferably a primary or a secondary alcohol.

If the alcohol is a primary alcohol, it often contains a stereogenic centre in 2- or 3-position.

The alcohol can contain substituents such as aryl groups, double bonds or preferably triple bonds, cycloaliphatic groups and preferably heterocyclic groups, functional groups as described before or halogens. Particular examples of primary alcohols are selected from (optionally substituted) phenyl ethanol, 1-octyne-3-ol and 1-butyne-3-ol.

In a particular embodiment, the alcohol is an aminoalcohol. In this case, the amino group is suitably present in 1-, 2- or 3-position relative to the hydroxyl group, preferably in 1- or 2-position. The amino group can be present as substituent or embedded in a heterocycle. Particular examples of aminoalcohols are select from 2-hydoxypiperidine and 2,2'-piperidineethanol.

In the process according to the invention, the mixture of enantiomers employed is preferably a racemic mixture. It can also be a mixture enriched in one of the enantiomers, which can be obtained, for example, by stereoselective reaction.

In stage (a) of the process according to the invention, the operation is often carried out in a basic reaction medium. The operation is preferably carried out in the presence of at least one base. Tertiary amine bases, such as, for example triethylamine or diisopropylethylamine, which comprise one basic functionality respectively, or N,N,N,N-tetramethylethylenediamine, which comprises 2 basic functionalities, are suitable in particular as base. Triethylamine is preferred.

The amount of base to be employed, if appropriate, depends on the amount of the reagent and on the number of basic functionalities in the base. The molar ratio of the reagent to the basic functionalities is generally at least 1. The ratio is generally at most 2. A ratio of 1 gives goods results.

Stage (a) of the process according to the invention is generally carried out in a solvent system in which the mixture of enantiomers and the reagent possess sufficient solubility and the functional group capable of reacting with the activated carboxyl group possesses sufficient nucleophilicity to react with the said group. Systems comprising at least one polar organic solvent are suitable, for example, as solvent system. Polar organic solvents which can be used are, for example, aliphatic or alicyclic ethers, such as diethyl ether, tetrahydrofuran or 1,4-dioxane, as well as aliphatic esters, such as, for example, ethyl acetate, which is preferred, aliphatic secondary amides, such as, for example, dimethylformamide and dimethylacetamide or, for example, N-methylpyrrolidone, or acetonitrile.

The amount of the reagent to be employed depends on the number of functional groups in the organic compound which are capable of reacting with the activated carboxyl group. Use is generally made of at least 1 molar equivalent of reagent per functional group capable of reacting with the activated carboxyl group. Use is generally made of at most 10 molar equivalents of reagent per functional group capable of reacting with the activated carboxyl group. Use is most often made of at most 5 molar equivalents of reagent per functional group capable of reacting with the activated carboxyl group. Use is preferably made of at most 3 molar equivalents of reagent per functional group capable of reacting with the activated carboxyl group. In a particularly preferred way, use is made of 1.1 to 2.5 molar equivalents of reagent per functional group capable of reacting with the activated carboxyl group.

In the process according to the invention, the time during which the reagent is reacted with the mixture comprising the enantiomers is generally less than or equal to 10 h. Most often, the time is less than or equal to 5 h. Preferably, the time is less than or equal to 3 h. Good results are obtained with a time of greater than of equal to 15 min. In practice, a time of greater than or equal to 30 min is generally applied. A time of 30 to 90 min is highly suitable.

The temperature at which, in stage (a), the reagent is reacted with the mixture comprising at least the enantiomers of an organic compound is generally less than or equal to 50° C. Most often, the temperature is less than or equal to 30° C. The temperature is generally greater than or equal to −30° C. Most often, the temperature is greater than or equal to −10° C.

In stage (b) of the process according to the invention, a mixture of diastereomers resulting from stage (a) is subjected to a separation operation, so as to obtain at least a first fraction composed essentially of a diastereomer. Separation operations which can be used for the separation of a mixture of diastereomers are known per se. Mention may be made, by way of examples, of distillation, crystallization and gas or liquid chromatography operations. Among these operations, crystallization and liquid chromatography operations, such as, for example, chromatography on a solid absorbent; such as alumina or silica, are preferred. Silica is particularly preferred as solid adsorbent.

In particular, the diastereomers obtained starting from an N-sulphonyl reagent give good preparative separation results by chromatography on silica, in particular on ungrafted silica.

In an alternative form of the process according to the invention, the mixture of diastereomers obtained is subjected to the separation operation without preliminary purification. The process and the reagent according to the invention make it possible not to isolate the crude mixture of diastereomers and to carry out the separation operation without preliminary purification.

On conclusion of stage (b), at least one fraction composed essentially of a diastereomer is obtained. Generally, the diasteromeric excess of this fraction is greater than or equal to 90%. The diasteromeric excess is often greater than or equal to 95%. Preferably, it is greater than or equal to 97%. It is even possible to achieve a diasteromeric excess of greater than or equal to approximately 99%.

In particular when the mixture of enantiomers employed in stage (a) is a racemic mixture, it is also possible to obtain in stage (b) a second fraction composed essentially of another diastereomer, often exhibiting a diasteromeric excess as defined above, which makes it possible to obtain the other enantiomer of the compound.

In stage (c) of the process according to the invention, at least a portion of the first fraction is subjected to a stage of cleavage of the carbonylic bond under conditions under which the protective group is essentially stable.

It is possible, for example, to carry out a hydrolysis or alcoholysis reaction as cleavage stage. A hydrolysis stage is preferred.

It has been found that it is possible, in particular when use is made of a reagent comprising a sulphonyl protective group, to selectively cleave the carbonylic bond of the diastereomer substantially without bringing about racemization in the protected enantiopure amino acid derivative or in the enantiopure compound released.

The term "conditions under which the protective group is essentially stable" is intended to denote in particular conditions under which the degree of deprotection (amount of protective group detrimentally changed with respect to the initial amount of protective group in the fraction) of the amino group is less than or equal to 20%. This degree is often less than or equal to 10%. Preferably, it is less than or equal to 5%. A degree of deprotection of less than or equal to 1% is more particularly preferred.

The cleavage stage is generally carried out at a temperature of greater than or equal to 60° C. This temperature is often greater than or equal to 70° C. A temperature of greater than or equal to 80° C. is preferred. The cleavage stage is generally carried out at a temperature of less than or equal to 150° C. This temperature is often less than or equal to 130° C. A temperature of less than or equal to 120° C. is preferred.

The cleavage stage is generally carried out at a pressure of greater than or equal to 1 bar (atmospheric pressure). A pressure of greater than or equal to 2 bar is preferred. The cleavage stage is generally carried out at a pressure of less than or equal to 30 bar. A pressure of less than or equal to 5 bat is preferred In a first alternative form of stage (c), the cleavage reaction is carried out in an acidic medium. This alternative form is particularly well suited when the carbonylic bond is an amide bond.

In this alternative form, use is advantageously made of an aqueous solution of an inorganic acid, such as sulphuric acid, phosphoric acid or halogen acids, such as, for example, hydrofluoric acid and hydrochloric acid. Hydrochloric acid is preferred.

If appropriate, the normality of the aqueous solution of mineral acid is generally at least 1N. The normality is often at least 2N. It is preferably at least 3N. The normality of the aqueous solution of mineral acid is generally at most 8N. The normality is often at most 6N. It is preferably at most 4N.

In a second alternative form of stage (c), the cleavage reaction is carried out in an alkaline medium. This alternative form is particularly well suited when the carbonyl bond is an ester or thioester bond.

In this alternative form, use is advantageously made of an aqueous solution of a base, such as sodium hydroxide, potassium hydroxide or sodium carbonate.

In this alternative form, the cleavage reaction is generally carried out at a pH of at least 9, preferably of at least 11. In this alternative form, the cleavage reaction is generally carried out at a pH of at most 13, preferably of at most 12.

An ester or a thioester, in particular a thioester, can optionally also be cleaved in a neutral or acidic aqueous medium.

In stage (d) of the process according to the invention, the enantiopure compound and an enantiopure derivative of the amino acid in which at least one amino group is protected by the protective group are recovered.

The recovery can be carried out, for example, by separation techniques as discussed above in the context of stage (b). In a preferred alternative form, the enantiopure derivative of the amino acid in which at least one amino acid group is protected is recovered by an extraction operation, for example with a solvent as described above in stage (a).

Good results are obtained, in particular for N-sulphonyl derivatives, with polar solvents, in particular esters, preferably ethyl acetate. The N-sulphonyl derivatives, in particular the N-arylsulphonyl derivatives, can, if necessary, easily be purified by crystallization.

Reagent can be regenerated starting from the enantiopure derivative of the amino acid recovered, for example by the activation methods discussed above.

The enantiopure derivative of the amino acid recovered can be reused and/or recycled, for example, in manufacturing reactions in accordance with stage (a), optionally after purification and/or activation.

In the preferred case of N-sulphonated pyroglutamic acid, the enantiopure derivative of the amino acid can be the corresponding N-sulphonated glutamic acid, which can be cyclised during the activation step, carried out e.g. with PC15.

In an alternative form of the process according to the invention, on conclusion of stage (b), at least a second fraction comprising at least one other diastereomer is additionally recovered, which fraction is subjected to a cleavage operation in accordance with stage (c), and an additional amount of enantiopure derivative of the amino acid and optionally a fraction enriched in the other enantiomer of the compound comprising a functional group capable of reacting with the activated carboxyl group are furthermore recovered.

The process and the reagent according to the invention can be used for the preparative or analytical separation of enantiomers. The process and the reagent are highly suitable for the preparative separation of enantiomers.

The invention also relates to the use of a reagent based on enantiopure glutamic or pyroglutamic acid, in which reagent at least one amino group of the amino acid is protected by a sulphonyl protective group as described above and in which reagent at least one carboxyl group of the amino acid is activated as described above, for the manufacture of an enantiopure compound comprising at least one functional group capable of reacting with the activated carboxyl group.

This reagent gave particularly good results for the economic preparation of enantiopure compounds.

The examples below are intended to illustrate the invention without, however, limiting it.

EXAMPLE 1

(2S)-1-Tosylpyroglutamyl chloride 48.2 g (0.15 mol, 1 eq.) of N$_\alpha$-tosyl-L-glutamic acid were dissolved in 400 ml of ethyl ether. The reaction medium was placed under nitrogen at 0° C. 94.9 g (0.45 mol, 3 eq.) of PCl$_5$ were then added at 0° C. The reaction medium was stirred at ambient temperature for 15 to 20 h.

The excess PCl$_5$ was subsequently filtered off through a sintered glass filter and 750 ml of petroleum ether were added to the filtrate. The mixture was placed in a refrigerator and a white solid precipitated. It was recovered by filtration (Yield: 80%).

EXAMPLE 2.1.

3-[5-(5S)-(1-Tosyl)-(2-pyrrolidonyl)]acetamide-3-phenyl-β-alanine

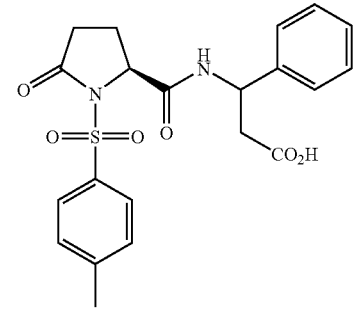

A solution of 911 mmol of persilylated D/L-3-amino-3-phenylpropionic acid in 130 ml of ethyl acetate was prepared by procedures analogous to Patent Application EP 184 243 on behalf of the Applicant Company.

25.6 g (83 mmol, 1 eq.) of (2S)-1-tosylpyroglutamyl chloride were dissolved in 130 ml of ethyl acetate. The solution was placed under nitrogen at 0° C.

The solution of silylated amino acid was then added and then 12.7 g (125 mmol, 1.5 eq.) of triethylamine in solution in 40 ml of ethyl acetate were also added. After approximately 30 min, the reaction was halted. The medium was washed with 200 ml of 5% aqueous KHSO$_4$ solution, then with 200 ml of 5% aqueous NaCl solution and finally with 200 ml of water.

The organic phase was evaporated to give an oil, which was taken up a first time in ethyl ether to precipitate a solid, which was filtered off on a Büchner funnel. This solid was again taken up in ethyl ether, which, after filtration, drying in an oven and milling, gave 31 g of a powder (Yield: 86%).

EXAMPLE 2.2.

3-[5-(5S)-(1-Tosyl)-(2-pyrrolidonyl)]acetamide-3-methyl-β-alanine

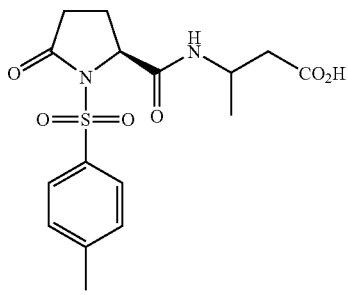

The procedure corresponded to that of Example 2.1 but the reaction was carried out starting from 600 mmol of DL-3-methyl-β-alanine. The yield obtained was 76%.

EXAMPLE 2.3.

2-[5-(5S)-(1-Tosyl)-(2-pyrrolidonyl)]acetamide-3-methylbutanoic acid

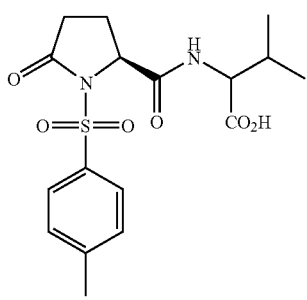

The procedure corresponded to that of Example 2.1 but the reaction was carried out starting from 70 mmol of DL-valine. The yield obtained was 84%.

EXAMPLE 2.4.

3-[5-(5S)-(1-Tosyl)-(2-pyrrolidonyl)]acetamide-proline

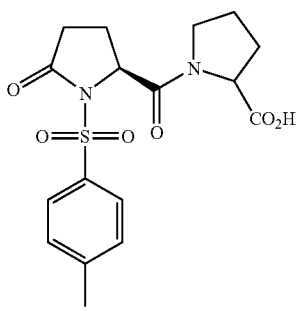

The procedure corresponded to that of Example 2.1 but the reaction was carried out starting from 70 mmol of DL-proline. The yield obtained was 84%.

EXAMPLE 2.5.

1-[5-(5S)-(1-Tosyl)-(2-pyrrolidonyl)]acetamide-(2'-(β-hydroxyethyl))-1-piperidine The procedure corresponded essentially to that of Example 2.1 but the reaction was carried out starting from a solution of 90 mmol of persilylated 2-(β-hydroxyethyl) piperidine in 100 ml ethyl acetate reacting with 81.8 mmol of reagent dissolved in 100 mL ethyl acetate and replacing the washing with KHSO4 by washing with NaHCO3. The yield obtained was 79%.

EXAMPLE 3.1.

Separation of diastereomers of 3-[5-(5S)-(1-tosyl)-(2-pyrrolidonyl)]acetamide-3-phenyl-β-alanine A diastereoisomeric mixture of 30 g of protected 3-amino-3-phenylpropionic acid obtained according to Example 2.1 was separated by MPLC on silica gel (stationary phase: Porasil 15-20 μm, mobile phase: ethyl acetate+0.1% acetic acid) to give 9 g of a diastereoisomer ($t_r$=4.30 min) with a d.e. (diasteriomeric excess) of 98.7% and 15 g of the other diastereoisomer ($t_r$=4.55 min) with a d.e. of 96.3%.

EXAMPLE 3.2.

Separation of diastereomers of 3-[5-(5S)-(1-tosyl)-(2-pyrrolidonyl)]acetamide-3-methyl-β-alanine A diastereoisomeric mixture of 17 g of protected 3-aminobutyric acid ($t_r$=3.00 and 3.25 min) obtained according to Example 2.2 was separated by reverse phase HPLC (stationary phase: Chromasil C18, mobile phase: water/acetonitrile/acetic acid gradient); 5.7 g of a diastereoisomer were obtained, with a d.e. of 97.7%, and 6.5 g of the other diastereoisomer, with a d.e. of 92.7%.

EXAMPLE 3.3.

Separation of diastereomers of 1-[5-(5S)-(1-Tosyl)-(2-pyrrolidonyl)]acetamide-(2'-(β-hydroxyethyl))-1-piperidine A diastereoisomeric mixture of 22.5 g of protected 2-(β-hydroxyethyl) piperidine obtained according to Example 2.5 was separated by column chromatography (stationary phase: Kromasil Sil 16 μm., mobile phase: 3% by volume isopropanol in isopropyl acetate); 4.5 g of a diastereoisomer with a d.e. of 98.9% tr 7.1 min and 8.5 g of the other diastereoisomer, with a d.e. of 93.9% tr 5.4 min, were obtained.

EXAMPLE 4.1.

Isolation of enantiopure 3-amino-3-phenylpropionic acid and recover of $N_\alpha$-tosyl-L-glutamic acid 3.3 g of the diastereoisomeric fraction with $t_r$=4.30 min recovered in Example 3.1 were treated in 100 ml of 4N hydrochloric acid in an autoclave at 120° C. for 16 h. 2.2 g of $N_\alpha$-tosyl-L-glutamic acid could thus be recovered by extraction with ethyl acetate (yield: 95%).

The 3-amino-3-phenylpropionic acid, present in the aqueous phase, was isolated in its neutral form after chromatography on Dowex AG 50 W $NH_4^+$ resin. 1.0 g of the D isomer was isolated, with an enantiomeric excess of 98.4% (yield: 79%).

The invention claimed is:

1. A process for the manufacture of an enantiopure compound comprising at least one functional group capable of reacting with an activated carboxyl group, starting from a mixture of enantiomers of the said compound, in which process;
   (a) a reaction medium comprising the mixture of enantiomers and an enantiopure amino acid reagent, in which at least one amino group is protected by a sulfonyl group and at least one carboxyl group is activated, is subjected to conditions appropriate for bringing about the reaction of the functional group with the activated carboxyl group, so as to form a carbonyl bond;
   (b) the mixture of diastereomers obtained is subjected to a separation operation, so as to obtain at least one fraction composed essentially of a diastereomer;
   (c) at least a portion of the said fraction is subjected to a stage of cleavage of the carbonyl bond under conditions under which the protective group is essentially stable; and
   (d) the enantiopure compound and an enantiopure derivative of the amino acid in which at least one amino group is protected by a sulfonyl group are recovered wherein the functional group capable of reacting with the activated carboxyt group is chosen from an amino group, which is optionally monoalkylated, a hydroxyl group or a thiol group.

2. The process according to claim 1, in which the activated carboxyl group is an acid halide or an anhydride.

3. The process according to claim 1, in which the carboxyl group is activated in situ.

4. The process according to claim 1, where in the enantiopure amino acid reagen is selected from the group consisting of alanine, valine, norvaline, leucine, norleucine, isoleucine, serine, isoserine, homoserine, threonine, allothreonine, methionine, ethionine, glutamic acid, pyroglutamic acid, aspartic acid, asparagine, cysteine, cystine, phenylalanine, tyrosine, tryptophan, lysine, arginine, histidine, ornithine, glutamine, citrulline, (1-naphthyl)alanine, (2-naphthyl)alanine, homophenylalanine, (4-chlorophenyl)alanine, (4-fluorophenyl)alanine, (3-pyridyl)alanine, phenylglycine, diaminopimelic acid (2,6-diaminoheptane-1,7-dioic acid), 2-aminobutyric acid, 2-aminotetralin-2-carboxylic acid, erythro-δ-methylphenylalanine, threo-δ-methylphenylalanine, (2-methoxyphenyl)alanine, 1amino-5-hydroxyindane-2-carboxylic acid, 2-aminoheptane-1,7-dioic acid, (2,6-dimethyl-4-hydroxyphenyl)alanine, erythro-δ-methyltyrosine and threo-δ-methyltyrosine.

5. The process according to claim 4, in which the reagent is based on (2S)-pyroglutamic acid.

6. The process according to claim 1, in which stage (a) is carried out in the presence of a base and at a temperature of −30 to +50° C.

7. The process according to claim 1, in which stage (b) is a crystallization operation or a chromatography operation.

8. The process according to claim 1, in which the carbonyl bond is an amide bond and the cleavage reaction is carried out in an acidic medium.

9. The process according to claim 8, in which use is made of an aqueous solution of an inorganic acid exhibiting a normality of 1 to 8N.

10. The process according to claim 8, in which the cleavage reaction is carried out at a temperature of 60 to 150° C.

11. The process according to claim 1, in which the compound comprising the functional group capable of reacting with the activated carboxyl group is an amino acid.

12. The process according to claim 11, in which the amino acid is a δ-amino acid.

13. The process according to claim 1, in which the carbonyl bond is an ester or thioester bond and the cleavage reaction is carried out in an alkaline medium.

14. The process according to claim 13, in which the cleavage reaction is carried out at a pHT of 8 to 12.

15. The process according to claim 13, in which the cleavage reaction is carried out at a temperature of 60 to 120° C.

16. The process according to claim 13, in which the compound comprising the functional group capable of reacting with the activated carboxyl group is an alcohol.

17. The process according to claim 1, in which, on conclusion of stage (b), at least one second fraction comprising at least one other diastereomer is additionally recovered, which fraction is subjected to a cleavage operation in accordance with stage (c), and an additional amount of enantiopure derivative of the amino acid and optionally a fraction enriched in the other enantiomer of the compound comprising a functional group capable of reacting with the activated carboxyl group are furthermore recovered.

18. The process according to claim 5, wherein the protective group is an arylsulphonyl group.

19. The process according to claims 1, in which reagent is regenerated starting from the enantiopure derivative of the amino acid recovered.

20. The process as claimed in claim 1 wherein said activated carboxyl group is an acid chloride and protective group is an alkylsulphonyl or an arylsulphonyl group.

* * * * *